United States Patent
Weaver et al.

(10) Patent No.: US 12,403,230 B2
(45) Date of Patent: Sep. 2, 2025

(54) PERITONEAL DIALYSIS SYSTEM WITH CONSTANT VOLUME DISPOSABLE PUMP

(71) Applicant: Fresenius Medical Care Holdings, Inc., Waltham, MA (US)

(72) Inventors: Colin Weaver, Pleasanton, CA (US); Nima Nouri, Pittsburg, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 918 days.

(21) Appl. No.: 17/563,651

(22) Filed: Dec. 28, 2021

(65) Prior Publication Data

US 2023/0201434 A1 Jun. 29, 2023

(51) Int. Cl.
*A61M 1/28* (2006.01)

(52) U.S. Cl.
CPC .............. *A61M 1/28* (2013.01); *A61M 1/282* (2014.02); *A61M 1/287* (2013.01); *A61M 2205/07* (2013.01); *A61M 2205/12* (2013.01); *A61M 2205/121* (2013.01); *A61M 2205/125* (2013.01); *A61M 2205/128* (2013.01); *A61M 2205/3334* (2013.01); *A61M 2205/3337* (2013.01)

(58) Field of Classification Search
CPC ........ A61M 1/28; A61M 1/282; A61M 1/287; A61M 2205/121; A61M 2205/125; A61M 2205/128; A61M 2205/3334; A61M 2205/3337; A61M 2205/07; A61M 2205/12

See application file for complete search history.

(56) References Cited

U.S. PATENT DOCUMENTS

| | | |
|---|---|---|
| 6,542,761 B1 | 4/2003 | Jahn et al. |
| 6,743,201 B1 | 6/2004 | Doing et al. |
| 7,648,627 B2 | 1/2010 | Beden et al. |
| 7,935,074 B2 | 5/2011 | Plahey et al. |
| 11,725,645 B2 | 8/2023 | Wilt et al. |
| 2004/0019313 A1 | 1/2004 | Childers et al. |
| 2006/0195064 A1 | 8/2006 | Plahey et al. |
| 2011/0028892 A1 | 2/2011 | Childers et al. |

(Continued)

FOREIGN PATENT DOCUMENTS

WO    WO 1986/001115    2/1986

OTHER PUBLICATIONS

"SleepSafe Technical Manual: Part No. 677 807 1," Fresenius Medical Care, Aug. 2000, 173 pages.

(Continued)

*Primary Examiner* — John Kim
(74) *Attorney, Agent, or Firm* — Fish & Richardson P.C.

(57) ABSTRACT

In one aspect, a peritoneal dialysis (PD) system includes a housing that receives a disposable cassette, a plurality of pinch valves that receive respective sections of fluid tubing of the disposable cassette, an air port that forms an airtight seal with an air line of the disposable cassette, an air pump that alternatingly pushes air out of the air port and pulls air in from the air port, and a computer processor that controls the plurality of pinch valves and the air pump such that the cassette performs a dwell phase in which the diaphragm pump pumps fresh dialysate from a dialysate bag to a heater bag, a fill phase in which the diaphragm pump pumps the fresh dialysate from the heater bag to a patient line, and a drain phase in which the diaphragm pump pumps spent dialysate form the patient to a drain.

11 Claims, 5 Drawing Sheets

(56) References Cited

U.S. PATENT DOCUMENTS

2016/0101278 A1 4/2016 Norris et al.
2019/0262525 A1 8/2019 Wyeth et al.

OTHER PUBLICATIONS

International Search Report and Written Opinion in International Appln. No. PCT/US2022/052857, mailed May 22, 2023, 20 pages.
International Preliminary Report on Patentability in International Appln. No. PCT/US2022/052857, mailed Jul. 11, 2024, 12 pages.

FIG. 4
(SECTION A-A)

FIG. 5
(SECTION A-A)

PERITONEAL DIALYSIS SYSTEM WITH CONSTANT VOLUME DISPOSABLE PUMP

TECHNICAL FIELD

The disclosure generally relates to dialysis machines, and more particularly to a peritoneal dialysis system.

BACKGROUND

Dialysis machines are known for use in the treatment of renal disease. The two principal dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. During peritoneal dialysis, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated peritoneal dialysis machines, called PD cyclers, are designed to control the entire peritoneal dialysis process so that it can be performed at home, usually overnight, without clinical staff in attendance.

A PD cycler may interact with a disposable cassette, which may contain one or more pumping chambers to drain and refill the patient's abdominal cavity with the dialysis solution, as well as valving elements (such as diaphragm valves) actuated by the PD cycler.

For example, U.S. Pat. No. 7,935,074, which is incorporated herein by reference, describes a PD cycler that uses a disposable cassette that controls fluid flows using pumps and air-actuated balloon valves. The pumps are actuated by a stepper motor that moves a pump head relative to a pumping chamber. As part of the pump control, the PD cycler uses an encoder and an end of travel switch for positional feedback for the pump head. The PD cycler utilizes six fluid-processing sequences: flush, prime, drain, fill, pause and dwell. The purpose of the flush sequence is to remove air from all the lines (except the patient line) and from the cassette. This is accomplished by pumping dialysate solution through the lines to be flushed. The prime sequence removes air from the patient line by pumping dialysate solution through the patient line. The drain sequence is used to pump dialysate solution from the patient to the drain. The fill sequence is used to pump dialysate solution from the heater bag to the patient. The pause sequence allows the patient to disconnect from the PD machine once the patient has been filled with dialysate solution. While the patient is disconnected from the machine, the machine transfers dialysate solution from solution bags to the heater bag. Finally, the dwell sequence is used to allow the dialysate solution to remain for a set time in the patient. Dwell sequences are identical to pause sequences with the exception that the patient does not disconnect from the machine. While a dwell sequence is occurring, the machine transfers dialysate solution from the solution bags to the heater bag.

PD systems such as described in U.S. Pat. No. 7,935,074 are complex and often correspondingly costly. Moreover, PD cyclers that utilize complicated pneumatic system (compressor, reservoir, tubing, fittings, pump assembly, etc.) can be noisy and in some cases have high failure rates and/or high maintenance costs. Noise levels may be attributed to the use of stepper motors, high pressure pumps (due to high operating pressures), and air operated balloon valves.

It is therefore an object of the present invention to provide a less complex system that maintains the same or analogous functions of such PD systems, while reducing noise and increasing reliability.

It is with respect to these and other considerations that the present improvements may be useful.

SUMMARY

This disclosure relates to peritoneal dialysis cyclers and related disposable components.

In one aspect, a peritoneal dialysis system includes a housing configured to receive a disposable cassette, a plurality of pinch valves configured to receive respective sections of fluid tubing of the disposable cassette, an air port configured to form an airtight seal with an air line of the disposable cassette, an air pump configured to alternatingly push air out of the air port and pull air in from the air port, and a computer processor configured to control the plurality of pinch valves and the air pump such that the cassette performs (a) a dwell phase in which the diaphragm pump pumps fresh dialysate from a dialysate bag to a heater bag, (b) fill phase in which the diaphragm pump pumps the fresh dialysate from the heater bag to a patient line, and (c) a drain phase in which the diaphragm pump pumps spent dialysate form the patient to a drain.

In some examples, the processor is configured to alternate between respective fluid flow paths of the dwell phase, the fill phase, and the drain phase solely by altering which subset of pinch valves is in an open state while the remainder of the pinch valves are in a closed state.

In some examples, the processor is configured to pump the fresh dialysate and the spent dialysate during the dwell phase, the fill phase, and the drain phase by controlling only the air flow into and out of the air port.

In some examples, the air pump is a piston pump.

In some examples, the peritoneal dialysis system further includes a second air port configured to form an airtight seal with a second air line of the disposable cassette. In some examples, the processor is configured to control air flow into and out of the second air port during the dwell phase, the fill phase, and the drain phase.

In some examples, processor is further configured to calculate, based on a constant volume pumped by the pump and a number of pump cycles, at least one of (a) a volume of pumped dialysate and (b) a flow rate of pumped dialysate.

In some examples, the peritoneal dialysis system includes the disposable cassette, which may include a diaphragm pump coupled to the air line and configured to be actuated by air alternatingly pushed out and pulled in through the air port by the air pump, and portions of flexible tubing positioned and configured to mate with respective pinch valves of the plurality of pinch valves when the disposable cassette is received by the housing, such that the pinch valves are controllable by the processor to open and close flow through the respective portions of flexible tubing.

In some examples, the disposable cassette further includes a first check valve disposed upstream of the diaphragm pump, and a second check valve disposed downstream of the diaphragm pump, such that the first and second check valves allow the diaphragm pump to pump fluid in only one direction.

In some examples, the peritoneal dialysis system includes a second air port, and the disposable cassette includes a second air line that forms an airtight seal with the second air port, and a second diaphragm pump, the first diaphragm pump and the second diaphragm pump being disposed in parallel flow paths.

In some examples, the air pump pumps air into the first diaphragm pump while simultaneously pulling air from the second diaphragm pump and pulls air from the first diaphragm pump while simultaneously pumping air into the second diaphragm pump.

In some examples, the air pump is a piston pump including a cylinder and a piston head, the air port is in fluid communication with an interior volume of the cylinder on a first side of the piston head, and the second air port is in fluid communication with an interior volume of the cylinder on a second side of the piston head, the second side being opposite the first side.

In another aspect, a disposable peritoneal dialysis cassette includes a constant volume pump having an inlet and an outlet; a pump inlet line to convey fluid to the inlet of the pump, a pump outlet line to convey fluid from the outlet of the pump, one or more solution lines to convey peritoneal dialysis fluid from a dialysis fluid source to the pump inlet line, a patient bag inlet line to convey the peritoneal dialysis fluid from the pump outlet line to a patient bag line, a patient bag outlet line to convey the peritoneal dialysis fluid from the patient bag line to the pump inlet line, a fresh dialysate line to convey the peritoneal dialysis fluid from the pump outlet line to a patient line, a spent dialysate line to convey spent peritoneal dialysis fluid from the patient line to the pump inlet line, a drain line configured to convey the spent peritoneal dialysis fluid from the pump outlet line to a drain. In some examples, each of the one or more solution lines, the patient bag inlet line, the patient bag outlet line, the fresh dialysate line, the spent dialysate line, and the drain line has a respective flexible tubing portion to be received by a respective pinch valve when the cassette is mounted to a peritoneal dialysis cycler.

In some examples, the pump is a diaphragm pump.

In some examples, the diaphragm pump attaches directly or indirectly to an air port of a peritoneal dialysis cycler when the cassette is mounted to the peritoneal dialysis cycler.

In some examples, the disposable peritoneal dialysis cassette further includes a first check valve disposed at or upstream of the inlet of the diaphragm pump, and a second check valve disposed at or downstream of the outlet of the diaphragm pump, such that the first and second check valves allow the diaphragm pump to pump fluid in only one direction.

In some examples, the disposable peritoneal dialysis cassette further includes a second diaphragm pump having an inlet and an outlet, a third check valve disposed at or upstream of the inlet of the second diaphragm pump, and a fourth check valve disposed at or downstream of the outlet of the second diaphragm pump, such that the third and fourth check valves allow the second diaphragm pump to pump fluid in only one direction, the pump inlet line forks to feed the first diaphragm pump and the second diaphragm pump in parallel, and fluid pumped from the outlet of the diaphragm pump and the second diaphragm pump converge in the pump outlet line.

In some examples, the disposable peritoneal dialysis cassette has an air bubble trap disposed along the pump inlet line.

In some examples, the air bubble trap includes a vent line having a hydrophobic filter to allow air from trapped air bubbles to escape from the vent line while preventing fluid from escaping the vent line.

In another aspect, a method of performing a peritoneal dialysis treatment using the peritoneal dialysis cassette includes performing a dwell phase by (a) closing or leaving closed pinch valves at the respective flexible tubing portions of the patient bag outlet line, the fresh dialysate line, the spent dialysate line, and the drain line, (b) opening or leaving open pinch valves at the respective flexible tubing portions of at least one of the one or more solution lines and the patient bag inlet line, and (c) operating the pump to pump fluid from a dialysis fluid source to a patient bag via the at least one of the one or more solution lines and the patient bag inlet line. In some examples, the method includes performing a fill phase by (a) closing or leaving closed pinch valves at the respective flexible tubing portions of the patient bag inlet line, the one or more solution lines, the spent dialysate line, and the drain line, (b) opening or leaving open pinch valves at the respective flexible tubing portions of the patient bag outlet line and the fresh dialysate line, and (c) operating the pump to pump the dialysis fluid from the patient bag to the patient via the patient bag outlet line and the fresh dialysate line. In some examples, the method further includes performing a drain phase by (a) closing or leaving closed pinch valves at the respective flexible tubing portions of the patient bag inlet line, the patient bag outlet line, the one or more solution lines, and the fresh dialysate line, (b) opening or leaving open pinch valves at the respective flexible tubing portions of and the spent dialysate line and the drain line, and (c) operating the pump to pump fluid from the patient to a drain via the spent dialysate line and the drain line.

In some examples, the pump pumps in the same direction during the dwell phase, the fill phase, and the drain phase.

In some examples, the method includes calculating, based on a constant volume pumped by the pump and a number of pump cycles, at least one of (a) a volume of pumped dialysate and (b) a flow rate of pumped dialysate.

Other aspects, features, and advantages will be apparent from the description, the drawings, and the claims.

DESCRIPTION OF DRAWINGS

Like reference symbols in the various drawings indicate like elements.

DETAILED DESCRIPTION

Figure 1:
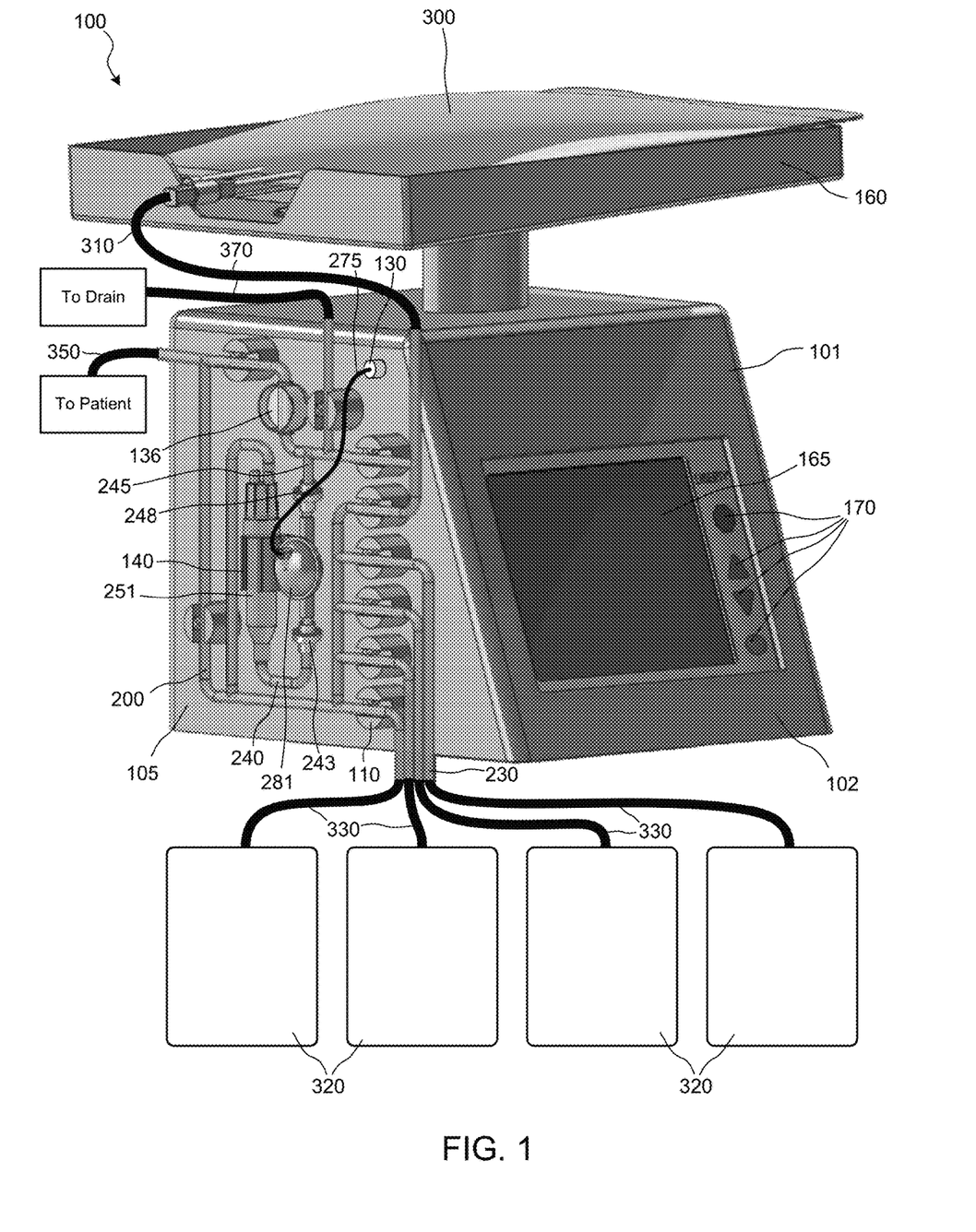
FIG. 1 shows an example peritoneal dialysis system.

Referring to FIG. 1, a PD system 100 includes a PD cycler (also referred to as a PD machine) 101. The PD cycler 101 includes a housing 102, a and a cassette interface 105 that mates with a disposable PD cassette 200. A heater tray 160 is positioned above the housing 102. The heater tray 160 is sized and shaped to accommodate a heater bag 300 for holding dialysis solution, which is heated via the heater tray 160. Although the heater tray 160 in this example is an external heater tray, it should be understood that other configurations, including an internal dialysate heater may be provided. The PD cycler 101 also includes a touch screen 165 and additional control buttons 120 that can be operated by a user (e.g., a patient or caregiver) to allow, for example, set-up, initiation, and/or termination of a PD treatment.

Dialysis solution bags 320, which may in some examples may be suspended from fingers on the sides of a cart, and a heater bag 300 is positioned on the heater tray 160. The dialysis solution bags 320 and the heater bag 300 are connected to the cassette 200 via dialysis solution bag lines 330 and a heater bag line 310, respectively. The dialysis solution bag lines 330 can be used to pass dialysis solution from dialysis solution bags 320 to the cassette 200 during use, and the heater bag line 310 can be used to pass dialysis solution back and forth between the cassette 200 and the heater bag 300 during use. In addition, a patient line 350 and a drain line 370 are connected to the cassette 200. The patient line 350 can be connected to a patient's abdomen via a catheter and can be used to pass dialysis solution back and forth between the cassette 200 and the patient during use. The drain line 370 can be connected to a drain or drain receptacle and can be used to pass dialysis solution from the cassette 200 to the drain or drain receptacle during use.

The cassette interface 105 includes a pump connection port 130, a plurality of valves, in this case pinch valves 110. The interface 105 also includes a pressure sensor 136, a holder 140 for holding a drip chamber or air trap of an inserted cassette, and a level sensor 145 for determining a fluid level in a drip chamber or air trap held in the holder 140.

The cassette 200 is shown in FIG. 1 without its body, or frame, to facilitate illustration of the other components of the cassette.

The cassette 200 includes a plurality of solution bag tubes 230 that are in fluid communication with respective fluid bag lines 300 and, therefore, the solutions contained in the respective solutions bags 320. In some examples, the solution bag tubes 230 are continuous extensions of the respective fluid bag lines 330, which are attached by connectors (e.g., luer or other suitable connectors) to the respective solution bags 320. In some examples, the solution bag tubes 230 are attached by connectors (e.g., luer or other suitable connectors) to the solution bag lines at the interface of the cassette.

The fluid bag tubes 230 are routed into respective pinch valves 110, which are operatively controllable to selectively open and close the fluid pathway through the respective fluid bag tubes 230. Following the pinch valves 110, the fluid bag tubes converge together into a pump inlet tube 240, which conveys fluids to an inlet of a pump 281, which during operation pumps the fluid into and through a pump outlet tube 245.

In this example, the pump 281 is a diaphragm pump, which works in conjunction with check valves 243 and 248, also known as one-way valves. Check valve 243 is disposed along the pump inlet tube 240 and prevents fluid from flowing in the direction from the pump to the solution bags 320, or any other points upstream of the check valve 243. Similarly, the check valve 248 is disposed along the pump outlet tube 245 and prevents fluid from flowing from any point downstream of the check valve 248 to the pump 281. Although the check valves in the illustrated example are separated from the pump 281 by portions of tubing, it should be understood that other examples may incorporate one or both of the check valves into the body of the pump 281.

To pump dialysis solution through the various fluid pathways, the pump 281 is actuated by alternatingly pushing and pulling air into and out of the pump 281 via an air line 275, which may be formed of any suitable tubing, and which attaches to the pump connection port 130. In other examples, the pump may be pressed directly onto a pressure connection port, thereby eliminating the air line 275.

As fluids are pumped through the pump outlet tube 245, the pump outlet tube branches off following the check valve 246 to different selectable flow paths depending on which combination of pinch valves 110 are controlled to be closed. In this illustrated example, the output of the pump may be selectably directed to the heater bag 300 via heater bag line 310, the patent via patient line 350, or the drain via drain line 370. In some examples, the drain line 370 and patient line 350 are continuous extensions of the respective branches of the pump outlet tube 330. In some examples, drain line 370 and patient line 350 are attached by connectors (e.g., luer or other suitable connectors) to the respective branches of the pump outlet tube at the interface of the cassette.

An air bubble trap 251 captures any air bubbles that might be present in the PD solution before it is pumped into the patient.

The various components and flow paths of the cassette and cassette interface may take various forms in different implementations. The configuration corresponding to that of FIG. 1 is shown in the flow chart of FIG. 2. As shown, the plurality pinch valves are implemented as valves 111, 112, 113, 114, 115, 116, 117, 118, and 119.

Figure 2:
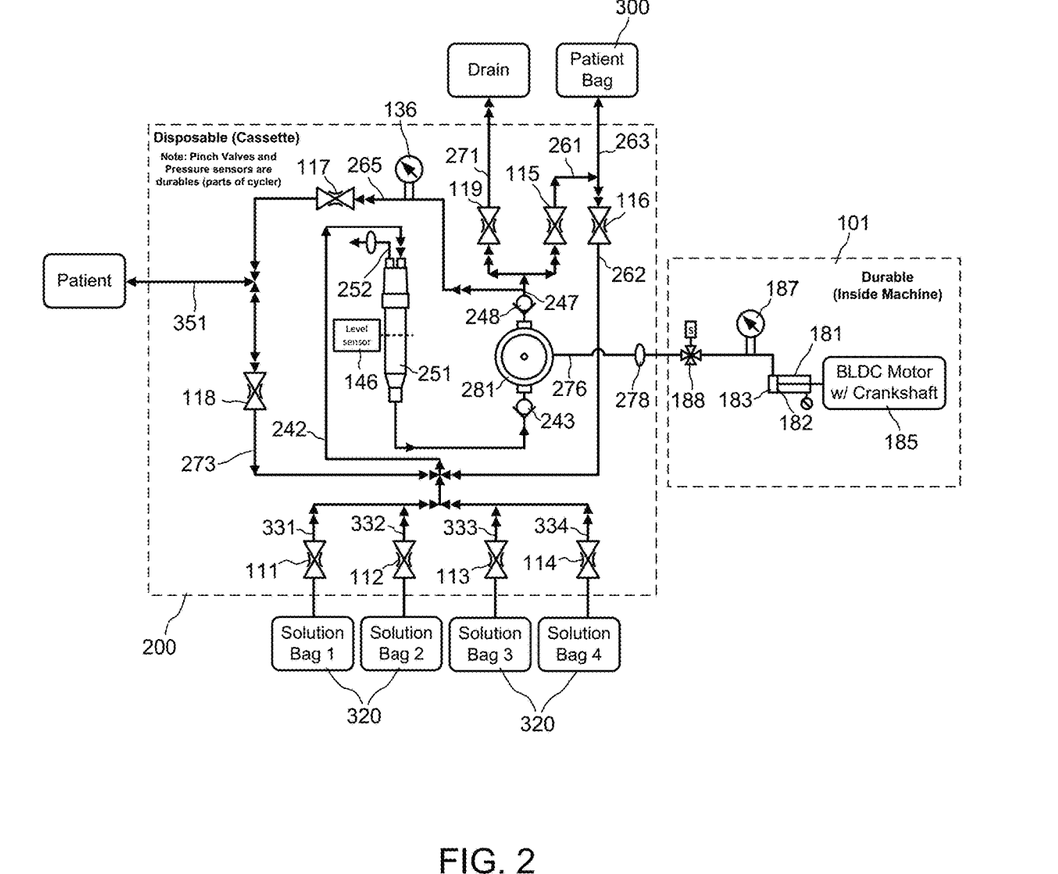
FIG. 2 is a flow diagram of an implementation of the peritoneal dialysis system of FIG. 1.

During operation, the heater bag 300, also referred to herein as a patient bag, is filled, e.g., during a "dwell phase," by closing each of pinch valves 116, 117, 118, 119, and any of the solution line pinch valves 111, 112, 113, and 114 from which fluid is not to be transferred. In this state, the patient bag inlet valve 115 plus one or more of the solution line valves 112, 113, and 114 are in an open state to allow the flow of solution fluid to flow from the selected solution bag or bags to the heater bag 300. For each solution bag 111, 112, 113, and 114 from which fluid is extracted, the fluid flows through a respective solution bag fluid line 331, 332, 333, and 334. Each of these lines 331, 332, 333, and 334 converges into a common pump inlet line 242 toward the diaphragm pump 281.

Along the pump inlet line 242 is disposed the air bubble trap 251. The air bubble trap 251 operates to capture any air bubbles in any of the various fluids that are pumped by the pump 281 in this example. The illustrated trap 251 includes a vent line 252 with a hydrophobic filter to allow air to be vented without any liquid escaping. If air from bubbles accumulates in the upper portion of the interior of the trap 251, at a certain point a level sensor generates an alert. This indicates to the operator of the machine, that air needs to be removed from the trap 251 so that the trap may continue to perform its function. The level sensor may be any suitable sensor, e.g., an optical sensor. In some examples, the triggering of the level sensor halts operation of the PD machine until air is removed.

After passing the trap 251 to remove any air bubbles, the fluid flows through a first check valve 243 and into the fluid side of the pump 281. This generally occurs as a result of negative pressure being exerted on the air side of the diaphragm inside the diaphragm pump 281. It should be understood, however, that in some examples, the fluid from the fluid bags may be gravity-fed or otherwise under positive pressure. In these cases, the pump 281 could draw in the fluid via reducing a positive air pressure on the air side.

A check valve 248 is provided downstream of the pump 281 to prevent any downstream fluid from being drawn back into the diaphragm pump 281 either during its intake stroke or any other time during operation.

After the diaphragm pump 281 has drawn in the fluid via inlet line 242, the machine pumps air into air side of the diaphragm pump 281. As this in turn pressures the fluid on the fluid side of the diaphragm, the fluid is prevented from escaping upstream by the check valve 243, thereby forcing the fluid into the pump outlet line 247 in the downstream direction as allowed by the check valve 248.

The pump outlet line 247 branches out into three separate lines—a patient bag inlet line 261, a patient fresh solution line 265, and a drain line 271. Each of these lines has a respective valve 115, 117, and 119. During the heater bag filling operation, the fresh dialysate valve 117, drain valve 119, and a heater bag outlet valve 116 are closed, and the heater bag inlet valve 115 is in an open state. Since the fresh dialysate valve 117 and the drain valve 119 are closed, the pressurized fluid exiting the pump 281 forces the fluid through the open heater bag inlet valve 115 and into the heater bag 300. This fluid pathway includes the heater bag inlet line 261 followed by a heater bag common line 263, which is in fluid communication with the heater bag 300, the heater bag inlet line 263, and a heater bag outlet line 263. To prevent the pumped fluid from flowing into the heater bag outlet line, a heater bag outlet valve 116 is also closed during this heater bag filling procedure.

To convey the heated dialysate to the patient during a "fill phase," all of the valves are closed except for the patient bag outlet valve 116 and the patient fresh dialysate valve 117, which are controlled to the open state. The diaphragm pump 281 is then operated in the same manner as during the heater bag filling. However, in this phase the pump draws the fluid from the heater bag 300, via heater bag common line 263 and heater bag outlet line 262, which then feed into the pump inlet line 242. Further, the fluid—in this case the heated dialysate—is pumped through the fresh dialysate line 265 as a result of the open state of the valve 117 together with the closed state of valves 115 and 119. The heated dialysate then flows through the patient line 351 and ultimately into the patient's abdominal cavity for the PD treatment.

A pressure sensor 136 monitors the pressure in the fresh dialysate line 265. This sensor can be analyzed by the electronic control system of the PD machine to determine that the pump 281 and check valves 243 and 248 are functioning properly. Further, by monitoring the pressure, the system can determine if there is an occlusion in the somewhere in the line, preventing or impeding fluid flow. Moreover, since the pressure sensor 136 is upstream of the pinch valve 117, and since the fresh dialysate line 265 is in communication with the pump outlet line 247, the pressure sensor 236 could be similarly monitored to assess operation and identify problems with the heater bag filling and spent dialysate draining functions.

In some implementations, the function of the valves 115, 117, and 119 and/or check valve 243 can be tested by closing each of valves 115, 117, and 119 and operating the pump 281 to pressurize fluid upstream of the valves. If, during this procedure, the pressure does not equalize to the pressure of air acting on the pump diaphragm, the system can recognize that one or more of the check valves 115, 117, and 119 and the check valve 243 is not functioning property. The system may then alert a user to manually check and correct any faulty components or connections before proceeding. Such pressure checks may be done before treatment or at any other appropriate time.

To drain the spent dialysate from the patient in a "drain phase," all of the valves are closed, except for patient outlet line valve 118 and drain valve 119. Again, the diaphragm pump operates in the same manner, but the fluid—in this case the spent dialysate—is pumped from the patient to the drain. Here, the spent dialysate flows from the patient through the patient line 351 and through a spent dialysate line 273, which conveys the spent dialysate to the pump inlet line 242. The dialysate then flows through the pump inlet line 242 into the pump 281, which pumps the dialysate through the pump outlet line 247 followed by the drain line 271, which then conveys the spent dialysate to the drain.

By utilizing a system of valves and shared flow lines into and out of the pump 281, this system allows a single pump to perform all fluid pumping operations (in this case, filling heater bag from solution bags, fresh dialysate from heater bag to patient, and spent dialysate from patient to drain) despite being configured to pump in a single direction as dictated by the check valves. Further, the use of check valves allows for a simplified disposable cassette, since the valves operate on the tubing itself, as opposed to requiring separate disposable valving components.

In the illustrated example, the diaphragm pump 281 is actuated by alternatingly pushing and pulling air from the air side of the pump via an air line 276. In this example, the pumping is effected by a piston pump 181. The piston pump 181 includes a piston 182 that reciprocates within a pump cylinder 183 to alternatingly push and pull air to and from the diaphragm pump 281. In this example, the piston is actuated by a brushless direct current motor with a crankshaft, but it should be understood that any suitable actuation mechanism may be implemented. For example, some examples utilize a series of stacked piezoelectric pumps to push and pull the air.

To monitor the air pressures generated by the pump 181, a pressure sensor 187 is provided. This sensor 187 sends signals to the electronics of the PD cycler 101. This signal is then processed to assess to proper functioning of the pump and other aspects of the system. For example, this signal may be compared with pressure sensed at pressure sensor 136 to assess proper function of valves 115, 117, and 119 and/or check valve 243 as discussed above.

A hydrophobic filter 278 is provided to prevent any liquid from being pulled into the interior of the machine 101 in the unlikely event of fluid getting into the air side of the diaphragm 285.

Also disposed along the air line on the machine-side is a 4-way, 3-position double solenoid valve 191, to allow for priming and syncing of the diaphragm 285 of pump 281 and the piston 182 of the piston pump 181 by venting or pulling in air as needed based on signals from pressure sensor 187. It should be understood, however, that other valving or priming/syncing mechanisms may be utilized in other examples.

Figure 3:
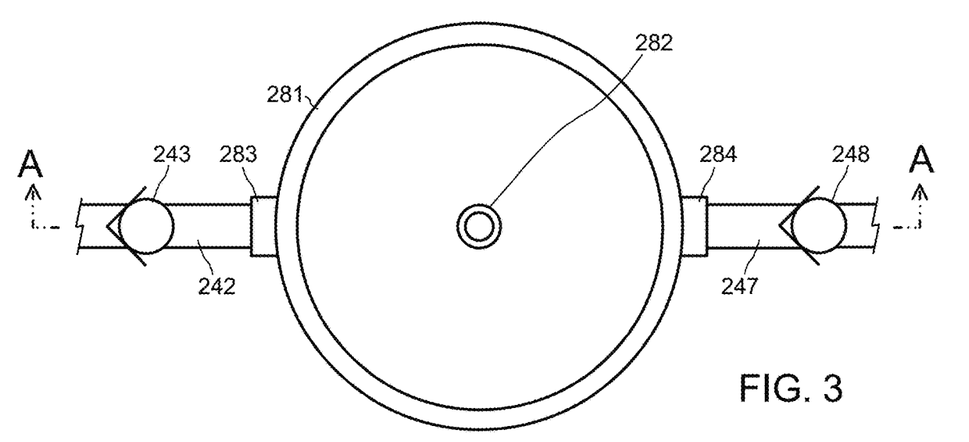
FIG. 3 is a top view of a portion of the cassette of FIG. 2.
Figure 4:
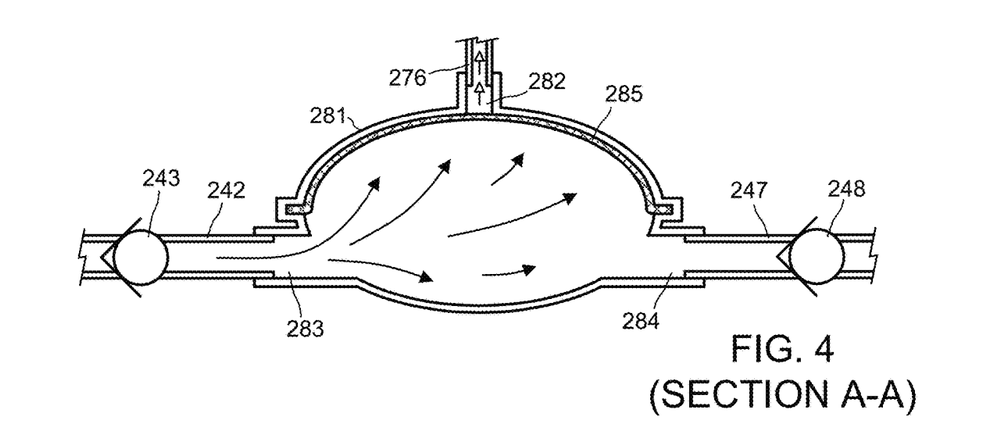
FIG. 4 is a sectional view of the portion of the cassette of FIG. 3 taken along section A-A when a pump diaphragm is in a first position.

FIGS. 3 to 4 show further detail of the diaphragm pump 281. The pump 281 includes an air line port 282 with an air-tight connection to air line 276. The pump 281 also includes a fluid inlet port in fluid-tight connection to pump inlet line 242, and a fluid outlet port 284 in fluid-tight connection to pump outlet line 247.

Figure 5:
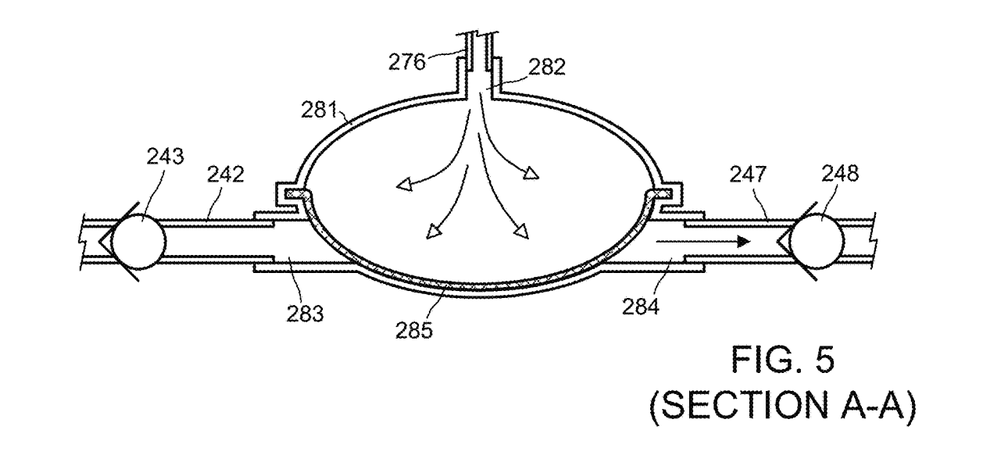
FIG. 5 is a sectional view of the portion of the cassette of FIG. 3 taken along section A-A when a pump diaphragm is in a second position.

A flexible diaphragm 285 separates an internal volume of the pump 281 between an air side and a fluid side. As shown in FIG. 4, the diaphragm 285 is in a fully retracted position, pulled against the interior wall of the pump 281 on the side containing air line port 282. FIG. 5 shows the diaphragm 285 in a fully extended position, pressed against the interior wall of the pump 281 opposite the air line port 282.

When the diaphragm 285 is in the fully extended position and air is allowed to leave the pump through the air line port 282 (via negative pumping pressure and/or other source of pressure differential), the diaphragm 285 moves from the fully extended position to the fully retracted position. Due to the movement of the diaphragm and orientation of the check valves 243 and 248, and as indicated by the arrows in FIG. 4, this fluid flows from the pump inlet line 242, through the fluid inlet port 283, and into the internal volume of the pump 281. This constitutes a fluid intake stroke.

After the fluid is drawn into the interior of the pump 281, the output stroke occurs. As the machine 101 pumps air into the pump via air line 276, the diaphragm 285 moves from the fully retracted position to the fully extended position. Since the check valves 243 and 248 allow flow in only one direction, this results in the fluid in the interior of the pump 281 being pushed outward through the fluid outlet port 284 and pump outlet line 247. This would them be followed by the next fluid intake stroke, as this cycle continues in sequence to effect the movement of the fluid through the various fluid lines as described herein.

The rigid interior walls of the housing of the pump 281 set a predefined and repeatable limit to the motion of the diaphragm between the fully retracted position and the fully extended position. As such, when the pump 281 operates by adequately pushing and pulling air from the air side, the pump outputs a constant volume per output stroke. This allows for accurate flow and volume measurements by the system 100 without requiring a separate flow sensor. For example, the processor of the system 100, or any other suitable processor, could calculate the volume pumped by multiplying the number of pump cycles by the constant volume known to be conveyed with each cycle. Similarly, the flow rate may be calculated by multiplying the frequency of the cycles by the constant volume pumped per cycle. This may likewise be done in examples, such as that described below in connection with FIG. 6, that have multiple pumps. In this regard, the pumped volume would be the sum of the volumes pumped by the multiple pumps and the flowrate would be the sum of the flow rates of the multiple pumps.

It should be appreciated that the presence of an air trap 251 upstream of the pump prevents air from entering the fluid side of the pump 281 via the fluid inlet line 242. Since the presence of air in the fluid side of the pod would alter the volume of fluid pumped per pumping cycle, this ensures that the aforementioned volume and flow sensing are feasible and accurate. Further, the air trap 251 ensures that air is not pumped through the system and ultimately to the patient.

A further advantage of the pump 281 is that it is non-invasive, in the sense that the dialysate on the fluid side of the pump is completely sealed from the air side of the pump, and therefore the air interface of the cycler. In the unlikely event of fluid getting into the air side of the diaphragm 285 due to break of the seal formed by the diaphragm, a hydrophobic filter 278 is provided along the air line to prevent any liquid from being pulled into the interior of the machine 101. Due to this isolation between the fluid and the air, and the pump being a disposable component as part of the cassette, this configuration eliminates any need for the cycler itself to be periodically sterilized.

Although the single pump 281 effectively moves fluid necessary for a PD treatment, the flow from the pump is cyclical, which pauses during the intake strokes. In some circumstances, it may be desirable to have a more continuous flow output. One way this may be accomplished is by adding a second pump 291, as illustrated in FIG. 6.

Figure 6:
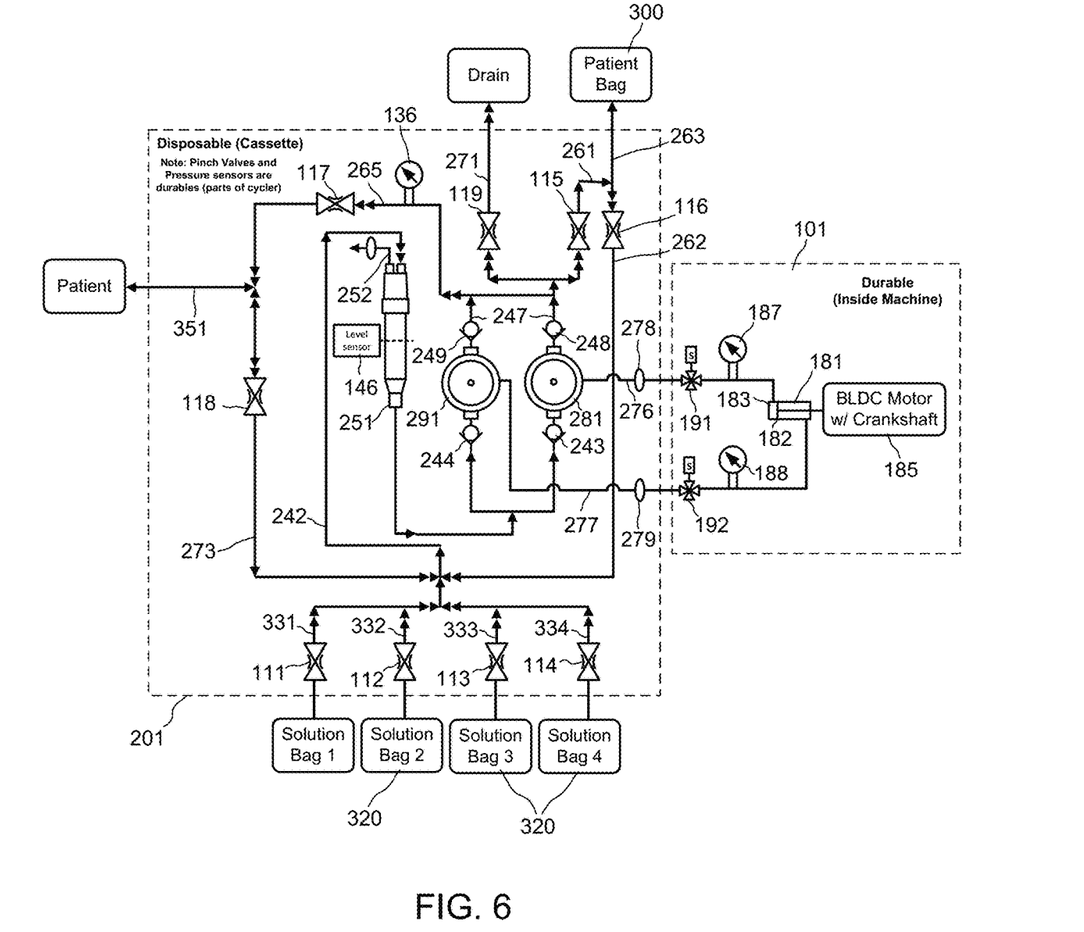
FIG. 6 is a flow diagram of an implementation of the peritoneal dialysis system of FIG. 1 with an alternative cassette.

In FIG. 6, the cassette 201 retains all of the features described above in connection with FIG. 2, but adds the second pump 291 that is the same as pump 281 other than operating out of phase with pump 281. Pump 291 is implemented by adding the pump 291 and corresponding check valves 244 and 249 in a flow line parallel to that of the first pump 291 and check valves 243 and 248. The second pump 291 is attached to a respective air line 277.

The air line 277 is attached to the piston pump cylinder 181 at an end opposite the attachment of air line 276. As such, as the piston moves in a first direction it pressurizes the air in air line 276 while simultaneously exerting negative pressure on the air in air line 277. When the piston then moves back in the second, opposite direction, it pressurizes the air in air line 277 while simultaneously exerting negative pressure on the air in air line 276. In this manner, the two pumps 281 and 291 operate 180 degrees out of phase, such that one is taking in fluid while the other is expelling fluid.

Associated with the second pump 291 are a second air pressure sensor 188, a second 4-way, 3-position double solenoid valve 192, and a second hydrophobic filter 279. These components perform the same function as the respective components 187, 191, and 278 described above, but with respect to the air and air line 277 associated with the second pump 291.

Figure 7:
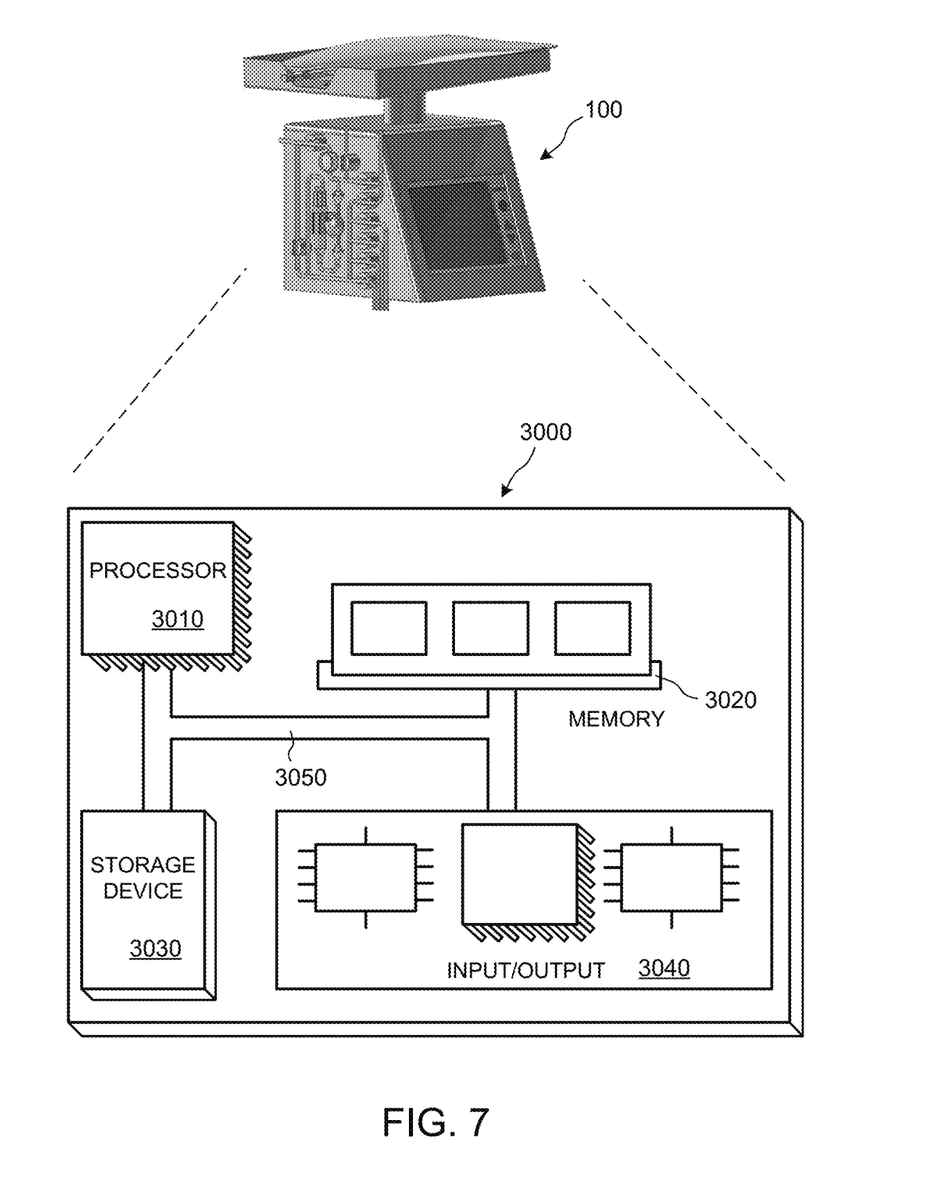
FIG. 7 is a block diagram of an example computer system by which a control unit of the peritoneal dialysis system of FIGS. 1 to 6 can be implemented.

FIG. 7 is a block diagram of an example computer system 3000 illustrated in connection with PD system 100. That is, the computer system 3000 is illustrative of computer systems that may be incorporated into PD system 100 described above, or any other implementations of the concepts set forth herein. The system 3000 includes a processor 3010, a memory 3020, a storage device 3030, and an input/output device 3040. Each of the components 3010, 3020, 3030, and 3040 can be interconnected, for example, using a system bus 3050. The processor 3010 is capable of processing instructions for execution within the system 3000. The processor 3010 can be a single-threaded processor, a multi-threaded processor, and/or other processor. Although "processor" may be used as a singular noun herein, including the claims, it should be understood that this term also encompasses multiple physical processors acting in coordination to perform the functions described. The processor 3010 is capable of processing instructions stored in the memory 3020 or on the storage device 3030. The memory 3020 stores information within the system 200. In some implementations, the memory 3020 is a computer-readable medium. The memory 3020 can, for example, be a volatile memory unit or a non-volatile memory unit. The processor 3010 executes the instructions to perform the various control functions described above (e.g., opening and closing the valves, analyzing pressure and level sensor readings, operating air pumps to actuate the diaphragm pump, calculating pumping rate and/or volume, etc. to perform the functions specified above, such as, e.g., the dwell phase, fill phase, and drain phase, causing information to be displayed on display 165, etc.). Execution of some of the instructions may be triggered by input signals from control buttons 170 and/or a touch interface of screen 165.

The storage device 3030 is capable of providing mass storage for the system 3000. In some implementations, the storage device 3030 is a non-transitory computer-readable medium. The storage device 3030 can include, for example, a hard disk device, an optical disk device, a solid-state drive, a flash drive, magnetic tape, or some other large capacity storage device. The storage device 3030 may alternatively be a cloud storage device, e.g., a logical storage device including multiple physical storage devices distributed on a network and accessed using a network. In some implementations, the information stored on the memory 3020 can also or instead be stored on the storage device 3030.

The input/output device 3040 provides input/output operations for the system 3000. In some implementations, the input/output device 3040 includes one or more of network interface devices (e.g., an Ethernet card), a serial communication device (e.g., an RS-232 10 port), and/or a wireless interface device (e.g., a short-range wireless communication device, an 802.11 card, a wireless modem (3G, 4G, 5G)). In some implementations, the input/output device 3040 includes driver devices configured to receive input data and send output data to other input/output devices, e.g., a keyboard, a printer, and display devices (such as the various controllable visual components described herein). In some implementations, mobile computing devices, mobile communication devices, and other devices are used.

In some implementations, the computer system 3000 is a microcontroller. A microcontroller is a device that contains multiple elements of a computer system in a single electronics package. For example, the single electronics package could contain the processor 3010, the memory 3020, the storage device 3030, and input/output devices 3040.

As used herein, an element or operation recited in the singular and preceded with the word "a" or "an" should be understood as not excluding plural elements or operations, unless such exclusion is explicitly recited. References to "one" embodiment or implementation of the present disclosure are not intended to be interpreted as excluding the existence of additional embodiments that also incorporate the recited features. Furthermore, a description or recitation in the general form of "at least one of [a], [b] or [c]," or equivalent thereof, should be generally construed to include [a] alone, [b] alone, [c] alone, or any combination of [a], [b] and [c].

A number of embodiments of the invention have been described. Nevertheless, it will be understood that various modifications may be made without departing from the spirit and scope of the invention. Accordingly, other embodiments are within the scope of the following claims.

What is claimed is:

1. A peritoneal dialysis system, comprising:
    a housing configured to receive a disposable cassette;
    a plurality of pinch valves configured to receive respective sections of fluid tubing of the disposable cassette;
    an air port configured to form an airtight seal with an air line of the disposable cassette;
    an air pump configured to alternatingly push air out of the air port and pull air in from the air port;
    a computer processor configured to control the plurality of pinch valves and the air pump such that the cassette performs (a) a dwell phase in which a diaphragm pump pumps fresh dialysate from a dialysate bag to a heater bag, (b) a fill phase in which the diaphragm pump pumps the fresh dialysate from the heater bag to a patient line, and (c) a drain phase in which the diaphragm pump pumps spent dialysate from the patient to a drain.

2. The peritoneal dialysis system of claim 1, wherein the processor is configured to alternate between respective fluid flow paths of the dwell phase, the fill phase, and the drain phase solely by altering which subset of pinch valves is in an open state while the remainder of the pinch valves are in a closed state.

3. The peritoneal dialysis system of claim 2, wherein the processor is configured to pump the fresh dialysate and the spent dialysate during the dwell phase, the fill phase, and the drain phase by controlling only the air flow into and out of the air port.

4. The peritoneal dialysis system of claim 1, wherein the air pump is a piston pump.

5. The peritoneal dialysis system of claim 1, further comprising a second air port configured to form an airtight seal with a second air line of the disposable cassette, wherein the processor is configured to control air flow into and out of the second air port during the dwell phase, the fill phase, and the drain phase.

6. The peritoneal dialysis system of claim 1, wherein the processor is further configured to calculate, based on a constant volume pumped by the diaphragm pump and a number of pump cycles, at least one of (a) a volume of pumped dialysate and (b) a flow rate of pumped dialysate.

7. The peritoneal dialysis system of claim 1, further comprising the disposable cassette, wherein the disposable cassette comprises:
    a diaphragm pump coupled to the air line and configured to be actuated by air alternatingly pushed out and pulled in through the air port by the air pump; and
    portions of flexible tubing positioned and configured to mate with respective pinch valves of the plurality of pinch valves when the disposable cassette is received by the housing, such that the pinch valves are controllable by the processor to open and close flow through the respective portions of flexible tubing.

8. The peritoneal dialysis system of claim 7, wherein the disposable cassette further comprises:
    a first check valve disposed upstream of the diaphragm pump; and
    a second check valve disposed downstream of the diaphragm pump, wherein the first and second check valves allow the diaphragm pump to pump fluid in only one direction.

9. The peritoneal dialysis system of claim 7, further comprising a second air port, wherein the disposable cassette further comprises
    a second air line configured to form an airtight seal with the second air port, and
    a second diaphragm pump, wherein the diaphragm pump and the second diaphragm pump are disposed in parallel flow paths.

10. The peritoneal dialysis system of claim 9, wherein the air pump is configured to pump air into the diaphragm pump while simultaneously pulling air from the second diaphragm pump and to pull air from the diaphragm pump while simultaneously pumping air into the second diaphragm pump.

11. The peritoneal dialysis system of claim 10, wherein
    the air pump is a piston pump including a cylinder and a piston head,
    the air port is in fluid communication with an interior volume of the cylinder on a first side of the piston head, and
    the second air port is in fluid communication with an interior volume of the cylinder on a second side of the piston head, the second side being opposite the first side.

* * * * *